US011426162B2

(12) United States Patent
Holsten

(10) Patent No.: US 11,426,162 B2
(45) Date of Patent: Aug. 30, 2022

(54) POWERED STAPLER HAVING VARYING STAPLE HEIGHTS AND SIZES

(71) Applicant: Covidien LP, Mansfield, MA (US)

(72) Inventor: Henry Holsten, Hamden, CT (US)

(73) Assignee: Covidien LP, Mansfield, MA (US)

( * ) Notice: Subject to any disclaimer, the term of this patent is extended or adjusted under 35 U.S.C. 154(b) by 249 days.

(21) Appl. No.: 16/832,105

(22) Filed: Mar. 27, 2020

(65) Prior Publication Data

US 2020/0246002 A1 Aug. 6, 2020

Related U.S. Application Data

(63) Continuation of application No. 15/906,062, filed on Feb. 27, 2018, now abandoned.

(51) Int. Cl.
*A61B 17/068* (2006.01)
*A61B 17/072* (2006.01)
(Continued)

(52) U.S. Cl.
CPC ....... *A61B 17/07207* (2013.01); *A61B 17/115* (2013.01); *A61B 2017/0046* (2013.01);
(Continued)

(58) Field of Classification Search
CPC ............ A61B 2017/07235; A61B 2017/07228
See application file for complete search history.

(56) References Cited

U.S. PATENT DOCUMENTS 3,499,591 A 3/1970 Green
3,771,526 A 11/1973 Rudie
(Continued)

FOREIGN PATENT DOCUMENTS

CN 201719302 U 1/2011
EP 0640315 A1 3/1995
(Continued)

OTHER PUBLICATIONS

European Office Action issued in European Patent Application No. 19159772.3, dated Jul. 1, 2020.
(Continued)

*Primary Examiner* — Eyamindae C Jallow
(74) *Attorney, Agent, or Firm* — Carter, DeLuca & Farrell LLP

(57) ABSTRACT

A loading unit of a powered surgical stapling instrument includes anvil and cartridge assemblies. The anvil assembly includes a first tissue contacting surface, and the cartridge assembly includes a second tissue contacting surface, a first plurality of staples, a second plurality of staples, and a plurality of pushers. The second tissue contacting surface defines a knife channel partitioning the second tissue contacting surface into first and second portions. Each of the first and second portions includes an inner tissue contacting surface and an outer tissue contacting surface. The inner tissue contacting surface defines a first row of retention slots. The inner tissue contacting surface and the first tissue contacting surface define a first tissue gap. The outer tissue contacting surface defines a second row of retention slots. The outer tissue contacting surface and the first tissue contacting surface define a second tissue gap larger than the first tissue gap.

14 Claims, 7 Drawing Sheets

(51) Int. Cl.
*A61B 17/115* (2006.01)
*A61B 17/00* (2006.01)

(52) U.S. Cl.
CPC .............. *A61B 2017/00398* (2013.01); *A61B 2017/00473* (2013.01); *A61B 2017/00477* (2013.01); *A61B 2017/07228* (2013.01); *A61B 2017/07235* (2013.01); *A61B 2017/07242* (2013.01); *A61B 2017/07257* (2013.01); *A61B 2017/07271* (2013.01); *A61B 2017/07285* (2013.01)

(56) References Cited

U.S. PATENT DOCUMENTS

| | | | |
|---|---|---|---|
| 4,305,539 A | 12/1981 | Korolkov et al. | |
| 4,319,576 A | 3/1982 | Rothfuss | |
| 4,429,695 A | 2/1984 | Green | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,767,044 A | 8/1988 | Green | |
| 4,809,695 A | 3/1989 | Gwathmey et al. | |
| 4,848,637 A | 7/1989 | Pruitt | |
| 4,930,503 A | 6/1990 | Pruitt | |
| 4,941,623 A | 7/1990 | Pruitt | |
| 4,978,049 A | 12/1990 | Green | |
| 5,027,834 A | 7/1991 | Pruitt | |
| 5,180,092 A | 1/1993 | Crainich | |
| 5,240,163 A | 8/1993 | Stein et al. | |
| 5,318,221 A | 6/1994 | Green et al. | |
| 5,342,396 A | 8/1994 | Cook | |
| 5,452,836 A | 9/1995 | Huitema et al. | |
| 5,452,837 A | 9/1995 | Williamson, IV et al. | |
| 5,480,089 A | 1/1996 | Blewett | |
| 5,484,095 A | 1/1996 | Green et al. | |
| 5,497,931 A | 3/1996 | Nakamura | |
| 5,533,521 A | 7/1996 | Granger | |
| 5,571,116 A | 11/1996 | Bolanos et al. | |
| 5,571,285 A | 11/1996 | Chow et al. | |
| 5,573,169 A | 11/1996 | Green et al. | |
| 5,667,526 A | 9/1997 | Levin | |
| 5,676,674 A | 10/1997 | Bolanos et al. | |
| 5,697,542 A | 12/1997 | Knodel et al. | |
| 5,709,680 A | 1/1998 | Yates et al. | |
| 5,865,361 A | 2/1999 | Milliman et al. | |
| 5,871,135 A | 2/1999 | Williamson IV et al. | |
| 5,915,616 A | 6/1999 | Viola et al. | |
| 5,964,394 A | 10/1999 | Robertson | |
| 6,202,914 B1 | 3/2001 | Geiste et al. | |
| 6,325,810 B1 | 12/2001 | Hamilton et al. | |
| 6,330,956 B1 | 12/2001 | Willinger | |
| 6,503,259 B2 | 1/2003 | Huxel et al. | |
| 6,669,073 B2 | 12/2003 | Milliman et al. | |
| 6,786,382 B1 | 9/2004 | Hoffman | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,044,352 B2 | 5/2006 | Shelton, IV et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,114,642 B2 | 10/2006 | Whitman | |
| 7,398,908 B2 | 7/2008 | Holsten et al. | |
| 7,401,721 B2 | 7/2008 | Holsten et al. | |
| 7,407,075 B2 | 8/2008 | Holsten et al. | |
| 7,455,676 B2 | 11/2008 | Holsten et al. | |
| 7,481,349 B2 | 1/2009 | Holsten et al. | |
| 7,588,174 B2 | 9/2009 | Holsten et al. | |
| 7,673,783 B2 | 3/2010 | Morgan et al. | |
| 7,721,930 B2 | 5/2010 | McKenna et al. | |
| 7,726,539 B2 | 6/2010 | Holsten et al. | |
| 7,832,611 B2 | 11/2010 | Boyden et al. | |
| 7,837,079 B2 | 11/2010 | Holsten et al. | |
| 7,837,081 B2 | 11/2010 | Holsten et al. | |
| 8,070,035 B2 | 12/2011 | Holsten et al. | |
| 8,113,406 B2 | 2/2012 | Holsten et al. | |
| 8,157,152 B2 | 4/2012 | Holsten et al. | |
| 8,317,070 B2 | 11/2012 | Hueil et al. | |
| 8,579,178 B2 | 11/2013 | Holsten et al. | |
| 8,806,973 B2 | 8/2014 | Ross et al. | |
| 8,840,004 B2 | 9/2014 | Holsten et al. | |
| 8,925,786 B2 | 1/2015 | Holsten et al. | |
| 9,055,943 B2 | 6/2015 | Zemlok et al. | |
| 9,192,387 B1 | 11/2015 | Holsten et al. | |
| 9,370,365 B2 | 6/2016 | Holsten et al. | |
| 9,662,111 B2 | 5/2017 | Holsten et al. | |
| 2003/0178465 A1 | 9/2003 | Bilotti et al. | |
| 2004/0004105 A1 | 1/2004 | Jankowski | |
| 2004/0232195 A1 | 11/2004 | Shelton et al. | |
| 2004/0232199 A1 | 11/2004 | Shelton et al. | |
| 2005/0006430 A1 | 1/2005 | Wales | |
| 2005/0006431 A1 | 1/2005 | Shelton et al. | |
| 2005/0006434 A1 | 1/2005 | Wales et al. | |
| 2005/0023324 A1 | 2/2005 | Doll et al. | |
| 2005/0070925 A1 | 3/2005 | Shelton et al. | |
| 2005/0070958 A1 | 3/2005 | Swayze et al. | |
| 2005/0173490 A1 | 8/2005 | Shelton | |
| 2005/0178813 A1 | 8/2005 | Swayze et al. | |
| 2005/0187576 A1 | 8/2005 | Whitman et al. | |
| 2005/0263562 A1 | 12/2005 | Shelton et al. | |
| 2006/0000868 A1 | 1/2006 | Shelton et al. | |
| 2006/0010406 A1 | 1/2006 | Lee et al. | |
| 2006/0022014 A1 | 2/2006 | Shelton et al. | |
| 2006/0022015 A1 | 2/2006 | Shelton et al. | |
| 2006/0025809 A1 | 2/2006 | Shelton | |
| 2006/0025810 A1 | 2/2006 | Shelton | |
| 2006/0025811 A1 | 2/2006 | Shelton | |
| 2006/0025812 A1 | 2/2006 | Shelton | |
| 2006/0025813 A1 | 2/2006 | Shelton et al. | |
| 2006/0025816 A1 | 2/2006 | Shelton | |
| 2006/0025817 A1 | 2/2006 | Ortiz et al. | |
| 2006/0049230 A1 | 3/2006 | Shelton et al. | |
| 2006/0097026 A1 | 5/2006 | Shelton | |
| 2006/0226196 A1 | 10/2006 | Hueil et al. | |
| 2007/0010838 A1 | 1/2007 | Shelton et al. | |
| 2007/0034667 A1 | 2/2007 | Holsten et al. | |
| 2007/0045379 A1* | 3/2007 | Shelton ............ A61B 17/07207 227/176.1 |
| 2007/0131732 A1* | 6/2007 | Holsten ................ A61B 17/068 227/179.1 |
| 2007/0262116 A1 | 11/2007 | Hueil et al. | |
| 2008/0078800 A1* | 4/2008 | Hess .................... A61B 17/072 227/175.1 |
| 2008/0078804 A1 | 4/2008 | Shelton et al. | |
| 2008/0210738 A1* | 9/2008 | Shelton ................ A61B 17/105 227/176.1 |
| 2010/0108740 A1 | 5/2010 | Pastorelli et al. | |
| 2012/0168487 A1 | 7/2012 | Holsten et al. | |
| 2012/0193398 A1* | 8/2012 | Williams ............ A61B 17/105 227/179.1 |
| 2013/0098965 A1 | 4/2013 | Kostrzewski et al. | |
| 2013/0334284 A1* | 12/2013 | Swayze ................ A61B 17/105 227/180.1 |
| 2014/0021239 A1 | 1/2014 | Kostrzewski | |
| 2014/0305988 A1 | 10/2014 | Boudreaux et al. | |
| 2015/0351765 A1 | 12/2015 | Valentine et al. | |
| 2017/0231628 A1* | 8/2017 | Shelton, IV ...... A61B 17/07207 227/180.1 |
| 2017/0231633 A1* | 8/2017 | Marczyk ................ A61B 17/32 227/175.2 |
| 2019/0059887 A1 | 2/2019 | Beardsley et al. | |

FOREIGN PATENT DOCUMENTS

| | | |
|---|---|---|
| EP | 0878169 A1 | 11/1998 |
| EP | 1090592 A1 | 4/2001 |
| EP | 1316290 A2 | 6/2003 |
| EP | 1479346 A1 | 11/2004 |

(56) References Cited

FOREIGN PATENT DOCUMENTS

| | | | |
|---|---|---|---|
| EP | 1621141 | A2 | 2/2006 |
| EP | 1728473 | A1 | 12/2006 |
| EP | 1754445 | A2 | 2/2007 |
| EP | 2111803 | A2 | 10/2009 |
| EP | 3225179 | A1 | 10/2017 |
| EP | 3446643 | A1 | 2/2019 |
| FR | 2838952 | A1 | 10/2003 |
| SU | 405234 | A1 | 9/1975 |
| SU | 1333319 | A2 | 8/1987 |
| SU | 1442191 | A1 | 12/1988 |
| SU | 1459659 | A1 | 2/1989 |
| WO | 8602254 | A1 | 4/1986 |
| WO | 9005489 | A1 | 5/1990 |
| WO | 9734533 | A1 | 9/1997 |
| WO | 03094743 | A1 | 11/2003 |
| WO | 03094746 | A1 | 11/2003 |
| WO | 03094747 | A1 | 11/2003 |

OTHER PUBLICATIONS

European Search Report for EP 06016963.8-2318 date of completion is Mar. 9, 2007 (9 pages).
International Search Report from EP Application No. 09 25 1067 dated Mar. 17, 2011.
European Search Report for corresponding EP 07 25 4366 date of completion is Nov. 11, 2010.
Partial European Search Report for Application No. 07 00 9831.4-2310 date of completion Jan. 27, 2011.
European Search Report dated Jul. 23, 2019, issued in EP Appln. No. 19159772.
European Office Action issued in European Patent Application No. 19159772.3, dated Jan. 29, 2021.

* cited by examiner

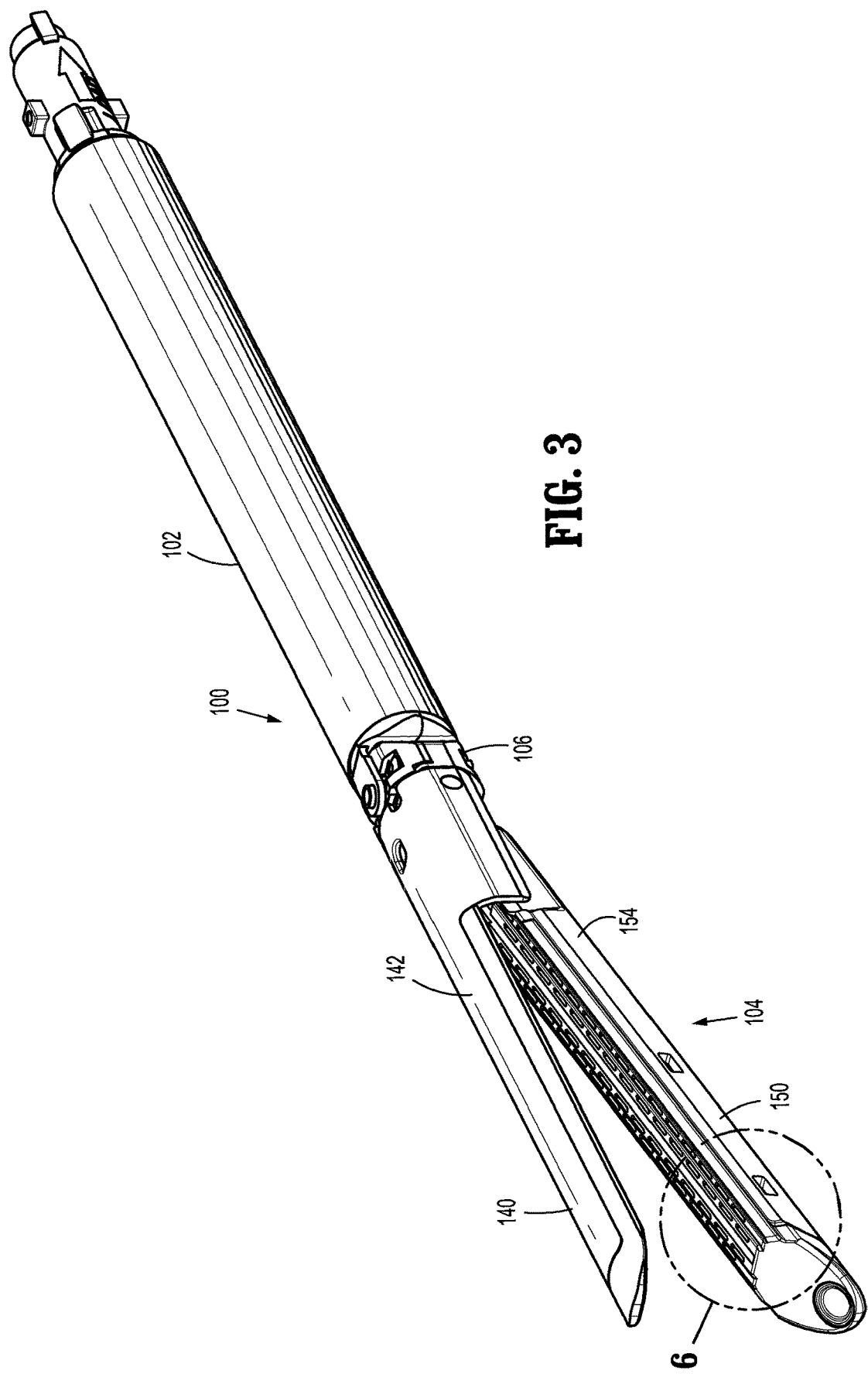

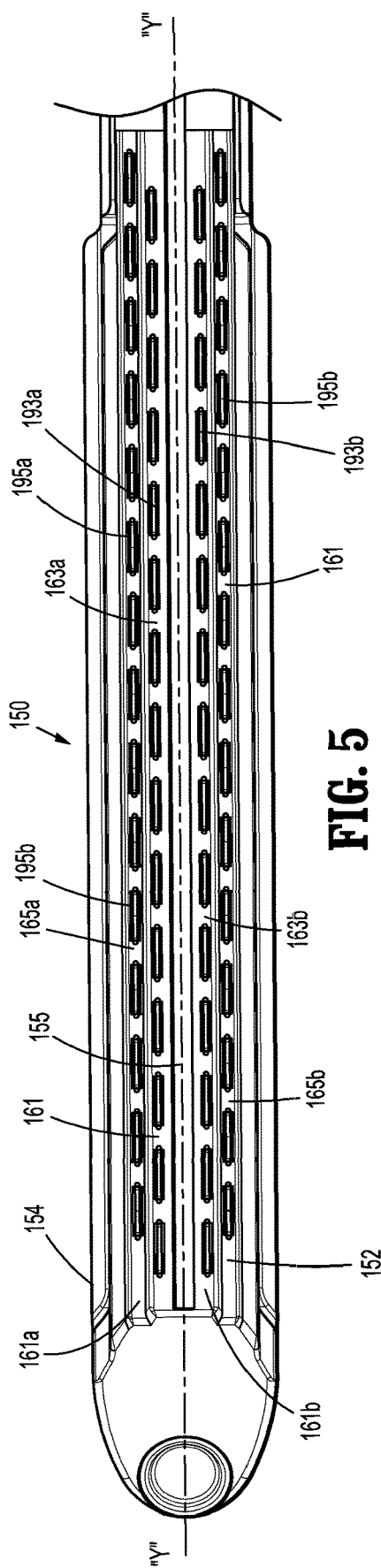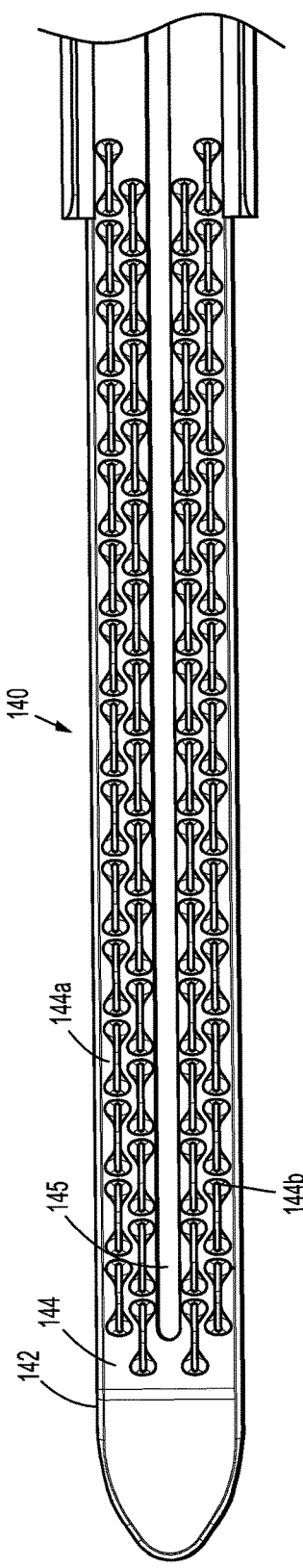

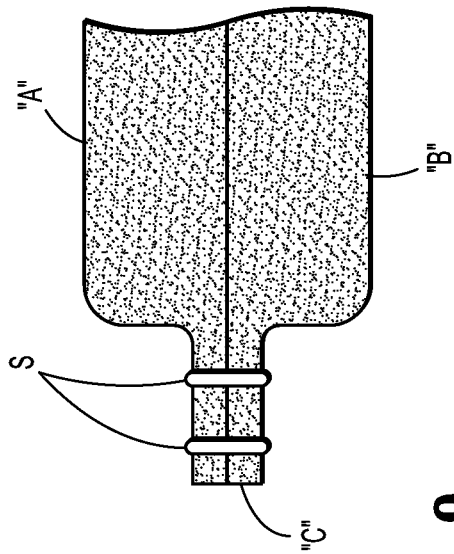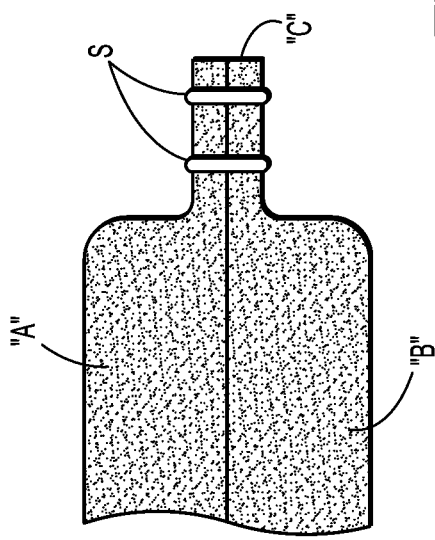
**FIG. 9
(Prior Art)**
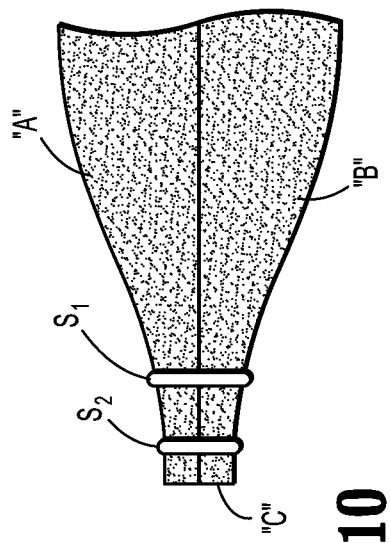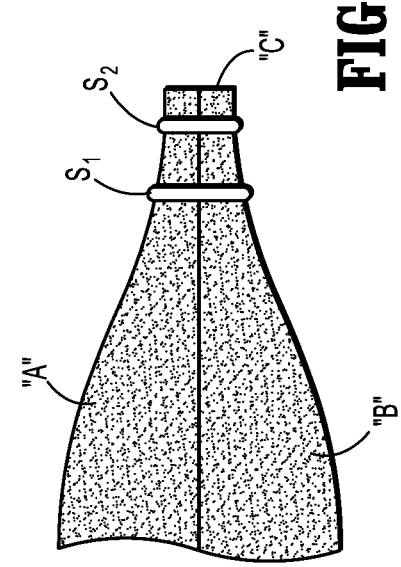
FIG. 10

POWERED STAPLER HAVING VARYING STAPLE HEIGHTS AND SIZES

CROSS-REFERENCE TO RELATED APPLICATION

This application is a continuation of U.S. patent application Ser. No. 15/906,062, filed on Feb. 27, 2018, the entire disclosure of which is incorporated by reference herein.

BACKGROUND

Technical Field

The present disclosure relates to surgical stapling instruments and, more particularly, to powered surgical stapling instruments including a loading unit configured to provide a variable pressure gradient to layers of tissue clamped between anvil and cartridge assemblies of the loading unit.

Background of Related Art

There are several known types of surgical stapling instruments specifically adapted for use in various procedures such as end-to-end anastomosis, gastrointestinal anastomosis, endoscopic gastrointestinal anastomosis, and transverse anastomosis. These surgical stapling instruments typically include a cartridge assembly and an anvil assembly. The cartridge assembly has one or more laterally spaced rows of staples which, depending on the particular stapling instrument, may be arranged in a linear or non-linear configuration. The anvil assembly includes staple forming depressions which are aligned with and/or in registration with the staple slots in the cartridge assembly. In use, each of the surgical stapling instruments involves gripping of tissue to be fastened, ejecting individual staples from the cartridge assembly through the gripped tissue, and forming the staples against the staple forming depressions of the anvil assembly.

A common issue in transecting tissue and/or in anastomosis procedures is achieving optimal balance between anastomotic strength and hemostasis. Therefore, a need exists for simple and effective powered surgical stapling instruments capable of improving the anastomotic strength and the degree of hemostasis when the layers of tissue are clamped and fastened between the anvil assembly and the cartridge assembly.

SUMMARY

The present disclosure is directed towards powered surgical stapling instruments configured to effectuate an improved balance between the anastomotic strength and the degree of hemostasis at the tissue interface. There is provided a powered surgical stapling instrument in accordance with an embodiment of the present disclosure. The powered surgical stapling instrument includes a powered handle assembly, a powered adapter assembly releasably secured to the powered handle assembly, and a loading unit releasably secured to the powered adapter assembly. The loading unit includes an anvil assembly and a cartridge assembly movable relative to the anvil assembly between open and approximated positions. The anvil assembly includes a first tissue contacting surface. The cartridge assembly includes a second tissue contacting surface, a first plurality of staples, a second plurality of staples, and a plurality of pushers.

The second tissue contacting surface defines a knife channel partitioning the second tissue contacting surface into first and second portions. The second tissue contacting surface is stepped. Each of the first and second portions includes an inner tissue contacting surface and an outer tissue contacting surface. The inner tissue contacting surface is disposed adjacent the knife channel. The inner tissue contacting surface defines a first row of retention slots. The inner tissue contacting surface and the first tissue contacting surface of the anvil assembly define a first tissue gap. The outer tissue contacting surface is disposed laterally outward of the respective inner tissue contacting surface and defines a second row of retention slots. The outer tissue contacting surface and the first tissue contacting surface of the anvil assembly define a second tissue gap larger than the first tissue gap.

The first plurality of staples has a first unformed leg length. The first plurality of staples is disposed in the first row of retention slots. The second plurality of staples has a second unformed leg length longer than the first unformed leg length. The second plurality of staples is disposed in the second row of retention slots. Each pusher of the plurality of pushers includes first and second panels configured to eject respective one of the first plurality of staples and one of the second plurality of staples through the second tissue contacting surface of the cartridge assembly.

In an embodiment, the first row of retention slots of the inner tissue contacting surface may be axially offset from the second row of retention slots of the outer tissue contacting surface.

In another embodiment, the first panel may have a height longer than the second panel.

In still another embodiment, each pusher of the plurality of pushers may further include a base panel interconnecting the first and second panels.

In still another embodiment, each of the first and second portions of the second tissue contacting surface of the cartridge assembly may include a transitioning portion interconnecting the respective inner and outer tissue contacting surfaces.

In yet another embodiment, the transitioning portion may define a slope configured to provide gradual compression on tissue when tissue is clamped between the anvil assembly and the cartridge assembly.

In still yet another embodiment, the first tissue contacting surface of the anvil assembly may be planar.

In still yet another embodiment, the first tissue contacting surface of the anvil assembly may define a longitudinal channel in registration with the knife channel of the cartridge assembly.

In still yet another embodiment, the inner and outer tissue contacting surfaces of the first and second portions of the second tissue contacting surface of the cartridge assembly may be symmetric with respect to the knife channel of the cartridge assembly.

In still yet another embodiment, the inner tissue contacting surfaces of the first and second portions of the second tissue contacting surface of the cartridge assembly may be coplanar. In addition, the outer tissue contacting surfaces of the first and second portions of the second tissue contacting surface of the cartridge assembly may be coplanar.

In still yet another embodiment, the outer tissue contacting surfaces may be parallel to the inner tissue contacting surfaces.

In still yet another embodiment, the second tissue contacting surface of the cartridge assembly and the first tissue contacting surfaces of the anvil assembly may define a varying tissue gap and may be configured to apply pressure to tissue disposed therebetween, wherein an amount of pressure applied to a portion of tissue disposed on the inner tissue contacting surface of the cartridge assembly is greater than an amount of pressure applied to a second portion of tissue disposed on the outer tissue contacting surface of the cartridge assembly.

In accordance with another embodiment of the present disclosure, there is provided a powered surgical stapling instrument including a powered handle assembly, a powered adapter assembly releasably secured to the powered handle assembly, and a loading unit releasably secured to the powered adapter assembly. The loading unit including an anvil assembly and a cartridge assembly. The anvil assembly includes a planar anvil surface defining a plurality of staple-forming depressions. At least one of the anvil assembly or the cartridge assembly is movable relative to the other between an open position and a pre-fire position. The cartridge assembly includes a tissue contacting surface, a first plurality of unformed staples, and a second plurality of unformed staples. The tissue contacting surface defines a knife channel partitioning the tissue contacting surface into first and second portions. The tissue contacting surface is stepped. Each of the first and second portions includes a first tissue contacting surface and a second tissue contacting surface. The first tissue contacting surface includes a first plurality of staple retention slots. The first tissue contacting surface and the planar anvil surface are configured to apply a first pressure to tissue disposed therebetween in the pre-fire position. The second tissue contacting surface defines a second plurality of staple retention slots. The second tissue contacting surface and the planar anvil surface are configured to apply a second pressure to tissue disposed therebetween in the pre-fire position. The second pressure is less than the first pressure. The first plurality of unformed staples has a first leg length. The first plurality of unformed staples is configured to be ejected through the first plurality of staple retention slots and into engagement with the plurality of staple-forming depressions of the anvil assembly to form a first plurality of formed staples. The second plurality of unformed staples has a second leg length. The second plurality of unformed staples is configured to be ejected through the second plurality of staple retention slots and into engagement with the plurality of staple-forming depressions of the anvil assembly to form a second plurality of formed staples. The second leg length is longer than the first leg length.

BRIEF DESCRIPTION OF THE DRAWINGS

The accompanying drawings illustrate embodiments of the disclosure and, together with a general description of the disclosure given above, and the detailed description of the embodiment(s) given below, serve to explain the principles of the disclosure, wherein:

FIG. 3 is a perspective view of the loading unit of the powered surgical stapling instrument of FIG. 1;

FIG. 4 is a partial, plan view of an anvil assembly of the loading unit of FIG. 2;

FIG. 5 is a partial, plan view of a cartridge assembly of the loading unit of FIG. 2;

FIG. 9 is a side view of a tissue/staple interface following a firing of a conventional surgical stapling instrument; and FIG. 10 is a side view of a tissue/staple interface following the firing of the powered surgical stapling instrument of FIG. 1.

DETAILED DESCRIPTION OF EMBODIMENTS

Figure 1:
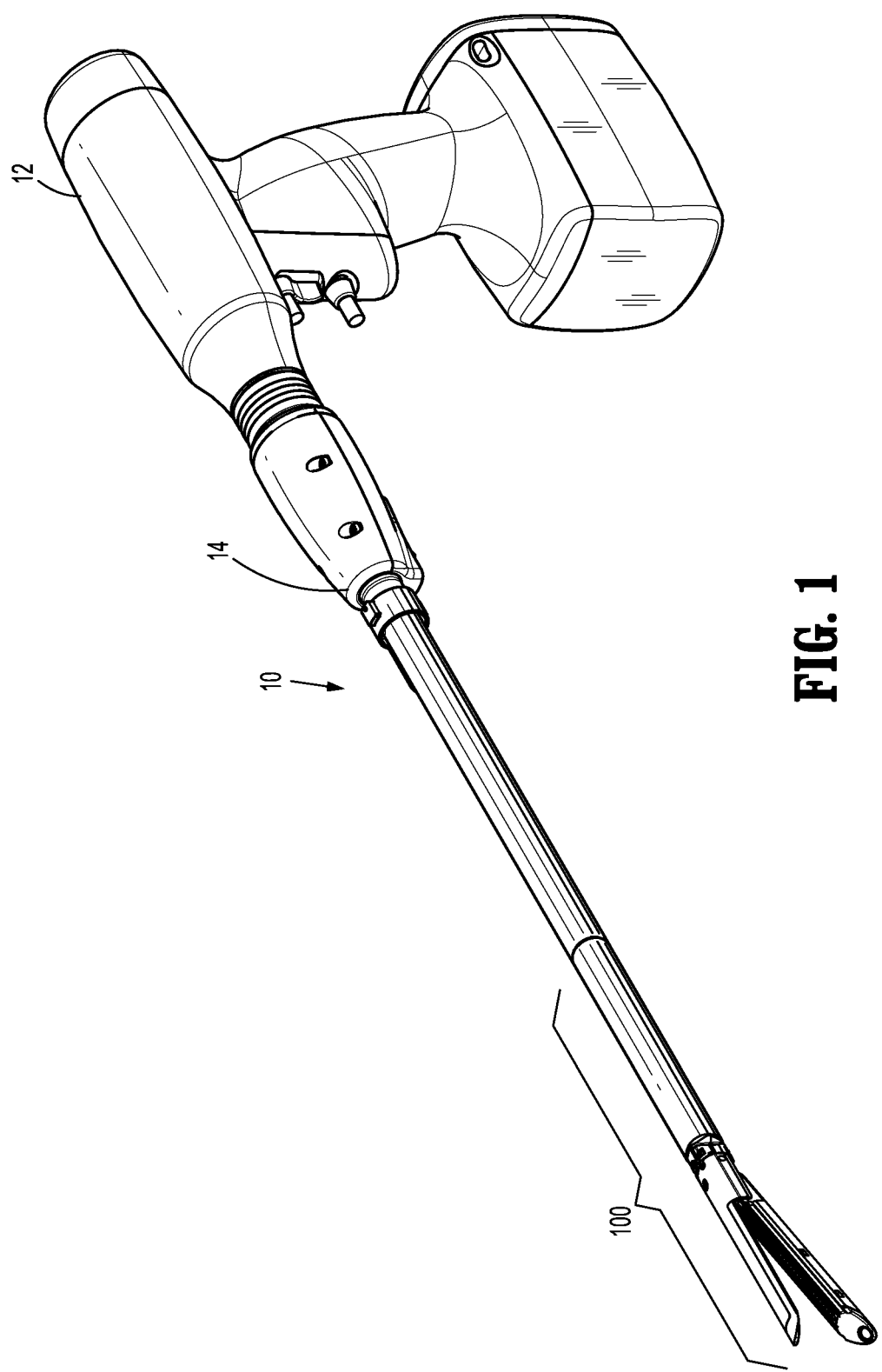
FIG. 1 is a perspective view of a powered surgical stapling instrument constructed in accordance with an exemplary embodiment of the present disclosure with a tool assembly in an open position.

Embodiments of the present powered surgical stapling instruments will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, a powered surgical stapler in accordance with embodiments of the present disclosure is generally shown as a surgical stapler 10. Surgical stapler 10 includes a powered handle assembly 12, a powered adapter assembly 14 releasably secured to powered handle assembly 12, and a loading unit 100 releasably secured to powered adapter assembly 14. Reference may be made to U.S. Pat. No. 9,055,943 ("the '943 patent") and U.S. Patent Application Publication No. 2016/0106406, the entire contents of each of which is incorporated herein by reference, for a detailed discussion of the construction and operation of exemplary powered handle and adapter assemblies. Alternatively, the device may be manually operated. Reference may be made to U.S. Patent Application Publication No. 2013/0098965, the entire contents of which is incorporated herein by reference, for a detailed discussion of the construction and operation of exemplary manually operated handle assemblies.

Figure 2:
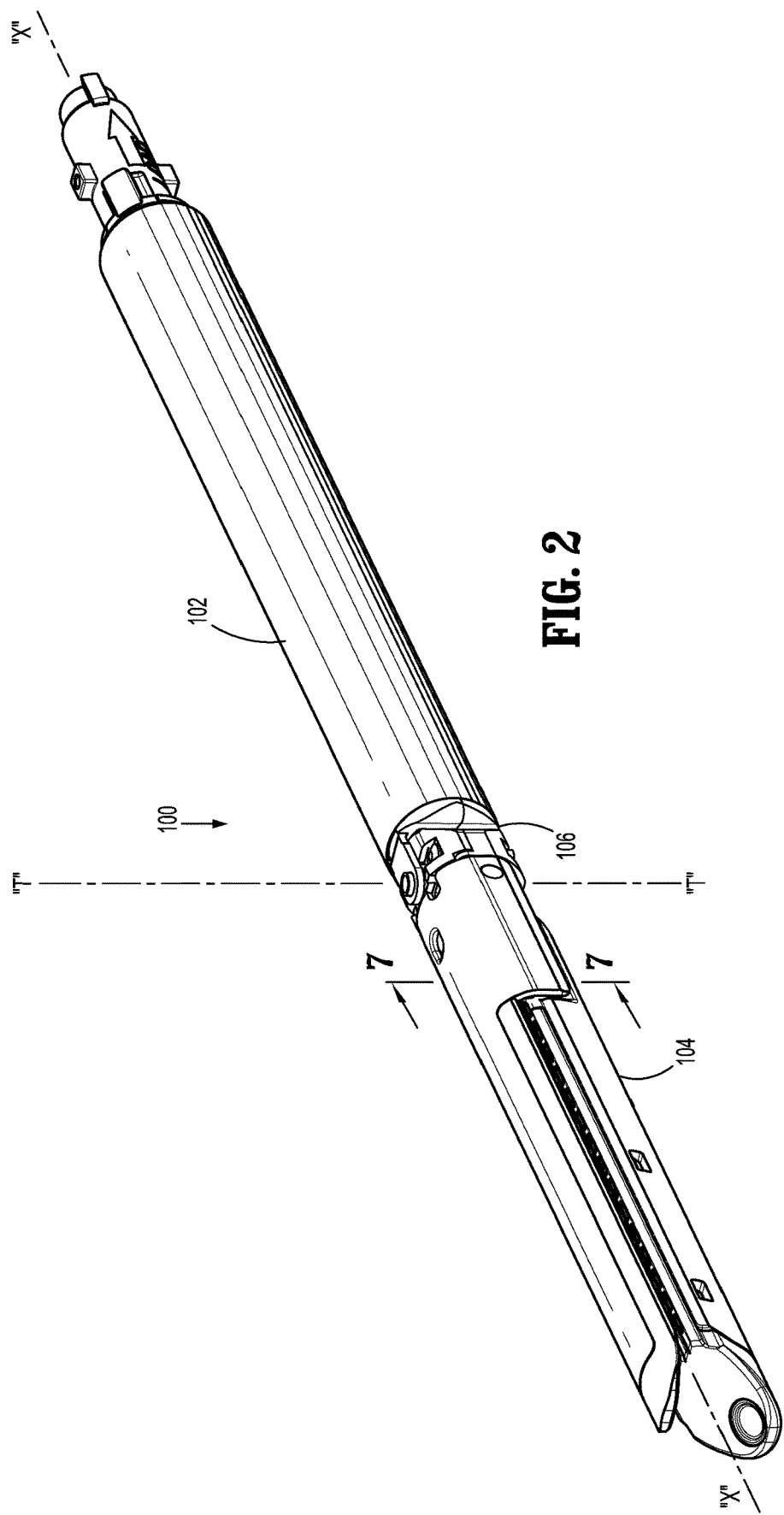
FIG. 2 is a perspective view of a loading unit of the powered surgical stapling instrument of FIG. 1 with the tool assembly in an approximated position.

With reference now to FIGS. 2 and 3, loading unit 100 of surgical stapler 10 includes a body portion 102 and a tool assembly 104. Body portion 102 is configured to be releasably coupled to powered adapter assembly 14 (FIG. 1). Tool assembly 104 includes an anvil assembly 140 and a cartridge assembly 150 that is movable in relation to anvil assembly 140 between open and approximated positions. A mounting assembly 106 is provided to couple tool assembly 104 to body portion 102 of loading unit 100. In embodiments, mounting assembly 106 couples tool assembly 104 to body portion 102 to facilitate pivotal movement of tool assembly 104 about an axis "T-T" transverse to a longitudinal axis "X-X" of body portion 102.

With reference to FIGS. 3 and 4, anvil assembly 140 includes an anvil body 142 and an anvil plate 144 secured to the underside of anvil body 142. In embodiments, anvil plate 144 includes a planar tissue contacting surface 144a that defines linear rows of staple forming depressions 144b. Alternatively, tissue contacting surface 144a of anvil plate 144 may be stepped or curved. Anvil assembly 140 may define a longitudinal slot 145 configured to receive a knife blade 157 (FIG. 7) therethrough.

Figure 7:
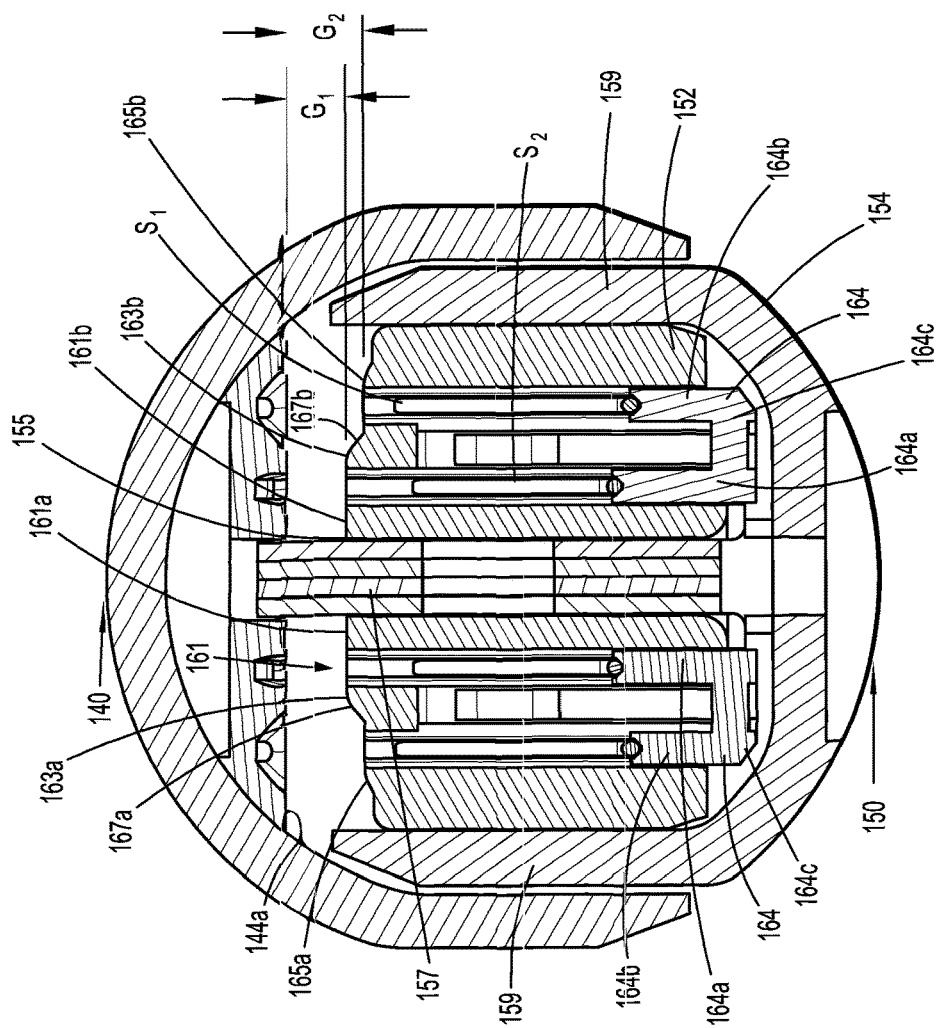
FIG. 7 is a cross-sectional view taken along section line 7-7 of FIG. 2.
Figure 6:
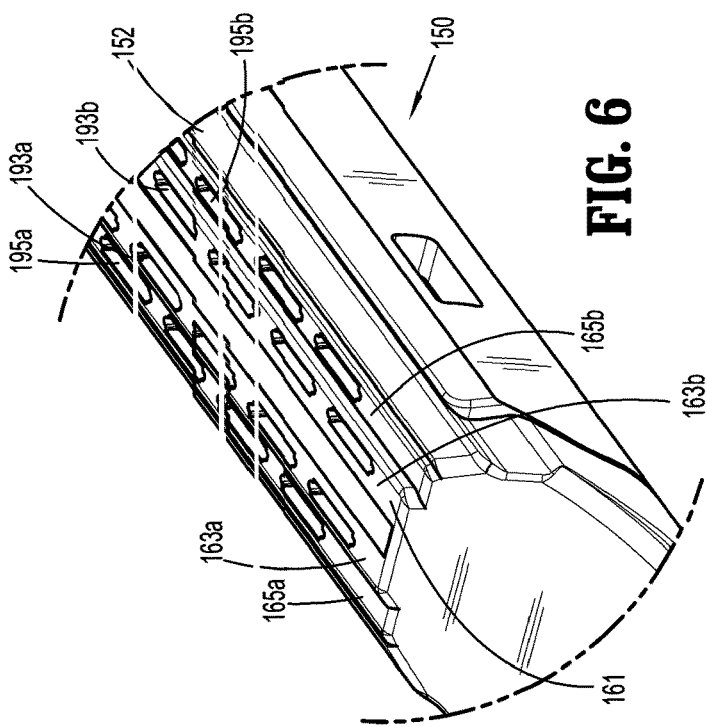
FIG. 6 is an enlarged view of the indicated area detail of FIG. 3.

With reference now to FIGS. 5-7, cartridge assembly 150 includes a cartridge body 154 and a staple cartridge 152 that may be removably received in cartridge body 154. Staple cartridge 152 includes a tissue contacting surface 161 configured to receive tissue thereon and defines a knife channel 155 configured to slidably receive a knife blade 157 (FIG. 7) and a drive beam (not shown). Knife channel 155 extends through tissue contacting surface 161 of staple cartridge 152 such that tissue contacting surface 161 is partitioned into first and second portions 161a, 161b. First and second portions 161a, 161b of tissue contacting surface 161 include respective inner tissue contacting surfaces 163a, 163b disposed adjacent knife channel 155, and outer tissue contacting surfaces 165a, 165b disposed laterally outward from the respective inner tissue contacting surfaces 163a, 163b. In embodiments, inner tissue contacting surfaces 163a, 163b are coplanar, and outer tissue contacting surfaces 165a, 165b are coplanar. Knife channel 155 may be centered on tissue contacting surface 161 such that inner and outer tissue contacting surfaces 163a, 163b, 165a, 165b on respective first and second portions 161a, 161b are symmetric with respect to knife channel 155. In embodiments, in the approximated position of tool assembly 104, tissue contacting surface 144a of anvil assembly 140 and inner tissue contacting surfaces 163a, 163b of cartridge assembly 150 define a first tissue gap $G_1$ (FIG. 7), and tissue contacting surface 144a of anvil assembly 140 and outer tissue contacting surfaces 165a, 165b of cartridge assembly 150 define a second tissue gap $G_2$ (FIG. 7) larger than first tissue gap $G_1$.

With particular reference to FIG. 7, tissue contacting surface 161 of staple cartridge 152 further includes transition portions 167a, 167b that interconnect the respective inner tissue contacting surfaces 163a, 163b and outer tissue contacting surfaces 165a, 165b. Transition portions 167a, 167b are sloped to provide gradual transition of compression force on tissue when tissue is clamped between anvil assembly 140 and cartridge assembly 150. Moreover, transition portions 167a, 167a direct fluid within tissue to flow laterally outward away from knife channel 150 when tissue is clamped between anvil assembly 140 and cartridge assembly 150.

In this arrangement, varying the size of tissue gaps between tissue contacting surface 161 of cartridge assembly 150 and tissue contacting surface 144a of anvil assembly 140 varies the amount of pressure applied to tissue disposed between tissue contacting surface 144a and tissue contacting surface 161 along a plane that is transverse to a longitudinal axis "Y-Y" (FIG. 5) of staple cartridge 152.

With continued reference to FIGS. 6 and 7, staple cartridge 152 defines a plurality of staple retention slots 193a, 193b, 195a, 195b (FIG. 6) extending through tissue contacting surface 161. Staple retention slots 193a, 193b are arranged in a linear fashion in respective inner tissue contacting surfaces 163a, 163b, and staple retention slots 195a, 195b are arranged in a linear fashion in respective outer tissue contacting surfaces 165a, 165b. In this manner, two linear rows of staple retention slots 193a, 193b, 195a, 195b are provided on each side of knife channel 155 in first and second portions 161a, 161b of tissue contacting surface 161. While it is envisioned that one or more additional rows of staple retention slots may be provided on tissue contacting surface 161, by providing two linear rows of staple retention slots 193a, 193b, 195a, 195b on each side of knife channel 155, the dimensions of cartridge assembly 150 and anvil assembly 140 are minimized to facilitate insertion of loading unit 100 through a small diameter incision or cannula and reduce patient trauma.

Staple retention slots 193a, 193b are axially offset from respective staple retention slots 195a, 195b. Staple retention slots 193a, 193b, 195a, 195b are in alignment with staple receiving depressions 144b (FIG. 4) defined in anvil plate 144. Each staple retention slot 193a, 193b, 195a, 195b is dimensioned to receive a respective surgical staple $S_1$, $S_2$ (FIG. 8) and a portion of a pusher 164. Surgical staples $S_1$, $S_2$ are supported on respective staple pushers 164 which are positioned to be engaged by a sled (not shown) such that longitudinal translation of the sled through cartridge body 154 urges pushers 164 towards the tissue contacting surface 161 of staple cartridge 152 to eject surgical staples $S_1$, $S_2$ out of respective staple retention slots 193a, 193b, 195a, 195b. See, e.g., U.S. Patent Application Publication No. 2013/0098965. If the closed or formed staple height is too high, then it may inadequately appose the tissues and result in leakage, bleeding, and/or dehiscence. Conversely, if the formed staple height is too low, then, e.g, ischemia or serosal shearing, may result, potentially leading to leakage or necrosis of tissue.

Figure 8:
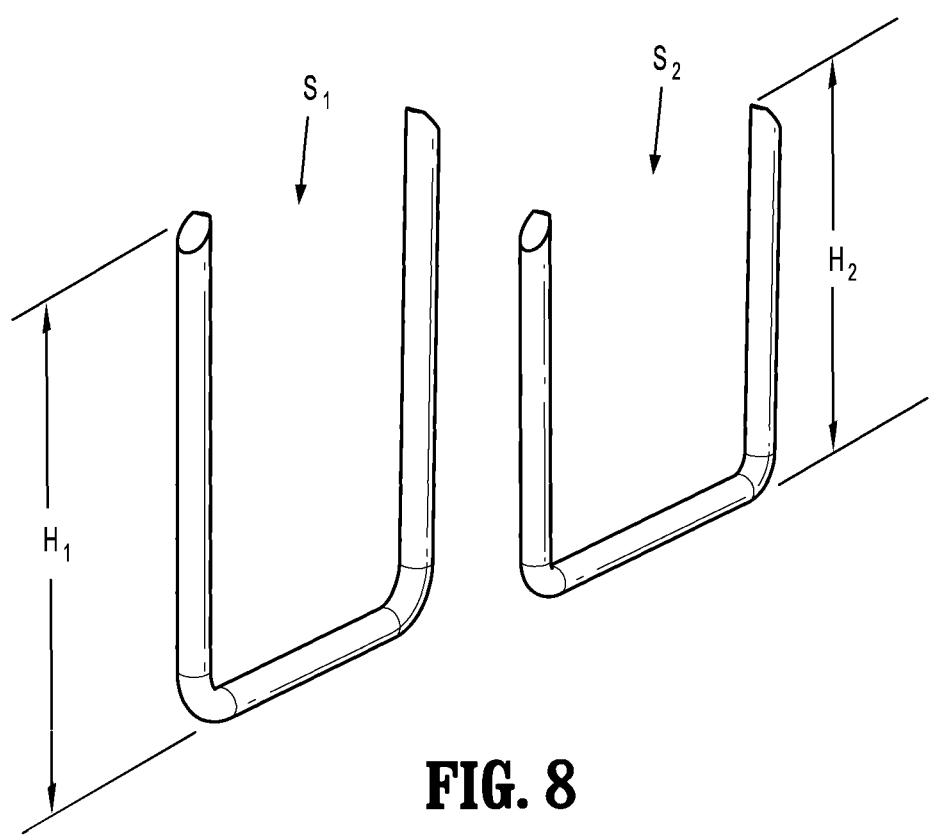
FIG. 8 is a perspective view of staples for use with the loading unit of FIG. 2.

With particular reference to FIGS. 6-8, staple retention slots 193a, 193b defined in inner tissue contacting surfaces 163a, 163b receive staple $S_2$ having a leg length of $H_2$ and staple retention slots 195a, 195b defined in outer tissue contacting surfaces 165a, 165b receive staple $S_1$ having a leg length of $H_1$ longer than $H_2$. For example, $H_1$ may be about 4.1 mm and $H_2$ may be about 3.5 mm. Alternatively, $H_1$ may be about 3.5 mm and $H_2$ may be about 2.3 mm. It is contemplated that surgical staples $S_1$, $S_2$ may be formed of a permanent or re-absorbable polymer. In addition, surgical staples $S_1$, $S_2$ may be formed of different materials. It is also contemplated that a diameter of the staple wire may vary in order to improve securement of surgical staples $S_1$, $S_2$ in tissue.

With particular reference back to FIG. 7, each pusher 164 includes a first panel 164a, a second panel 164b, and a base panel 164c interconnecting first and second panels 164a, 164b. First panel 164a is dimensioned to be received in a respective staple retention slot 193a, 193b, and second panel 164b is dimensioned to be received in a respective staple retention slot 195a, 195b. First panel 164a has a height larger than a height of second panel 164b to accommodate shorter surgical staples $S_2$.

The configuration of tissue contacting surface 161 of staple cartridge 152 causes a greater degree of compression to occur along inner tissue contacting surface 163a, 163b of cartridge assembly 150 adjacent knife channel 155. This greater degree of compression urges fluid stored in the layers of tissue adjacent knife channel 155 to flow laterally outward from knife channel 155. By reducing the amount of fluid retained in the layers of tissue on inner tissue contacting surface 163a, 163b, the overall thickness of the tissue layers decreases. The decrease in overall tissue thickness is such that surgical staple $S_2$ having a shorter leg length $H_2$ tightly fastens the layers of tissue adjacent knife channel 155 to inhibit leakage from the fastened tissue. The tissue gap $G_2$ increases towards outer walls 159 of cartridge body 154 as the amount of compression decreases, whereby surgical staples $S_1$ having a longer leg length $H_1$ less tightly fasten the layers of tissue on outer tissue contacting surfaces 165a, 165b. The reduced compression and reduced tightness of the staples $S_1$ outwardly of inner tissue contacting surfaces 163a, 163b allows a minimal amount of blood to flow past staples $S_1$ towards staples $S_2$ to reduce the likelihood of necrosis of tissue adjacent staples $S_1$. By inhibiting necrosis of tissue adjacent staples $S_1$, the strength of the tissue and thus, the staple line is improved.

In operation, after the layers of tissue are positioned between tissue contacting surface 161 of cartridge assembly 150 and tissue contacting surface 144a of anvil assembly 140, the actuation mechanism is actuated for sequentially ejecting surgical staples $S_1$, $S_2$ through respective staple retention slots 193a, 193b, 195a, 195b, whereby interaction between surgical staples $S_1$, $S_2$ and anvil assembly 140 forms completed surgical staples for joining the layers of tissue. In particular, an actuation sled (not shown) is positioned within the cartridge body 154 to pass longitudinally through cartridge body 154 into sequential engagement with pushers 164 to sequentially eject staples $S_1$, $S_2$ from cartridge body 154. Reference may be made to the '943 patent and also to U.S. Pat. No. 6,202,914, the entire contents of which is also incorporated herein by reference, for a detailed discussion of the construction and operation of the actuation mechanism including the sled (not shown) and pushers 164.

Tissue contacting surface 161 provides a variable pressure gradient (i.e. load profile) to tissue clamped between anvil assembly 140 and cartridge assembly 150. By providing a gradual compression gradient to the layers of tissue, a higher degree of hemostasis may be effected. The layers of tissue disposed on inner tissue contacting surfaces 163a, 163b are subject to higher compressive forces, which, in turn, forms thinner layers of tissue as compared to layers of tissue disposed on outer tissue contacting surfaces 165a, 165b. Since the layers of tissue on inner tissue contacting surfaces 163a, 163b can be compressed more, smaller sized surgical staple $S_2$ are used to staple the transected layers of tissue. When the surgical staples $S_1$, $S_2$ are deployed and formed in tissue, the smaller surgical staples $S_2$ are disposed adjacent the cut line in the tissue. Surgical staples $S_1$, which are the larger staples, are disposed laterally outward of surgical staples $S_2$. This arrangement provides improved hemostasis in the portion of tissue having surgical staples $S_2$ and further supports improved blood flow through tissue towards surgical staples $S_2$ to inhibit necrosis of tissue supporting the formed staples $S_2$.

With reference to FIGS. 9 and 10, when layers of tissue "A" and "B" are fastened using a conventional surgical stapler and conventional staples "S", there exists a sharp transition from the un-fastened layers of tissue to the fastened layers of tissue (FIG. 9). This may result in a greater load being placed on the layers of tissue and may produce an undesirable effect on the layers of tissue. In comparison, when layers of tissue "A" and "B" are fastened utilizing surgical stapler 10, the tissue interface has a substantially tapered profile (FIG. 10). The tissue interface has a gradual transition from the un-fastened layers of tissue to the fastened layers of tissue. This arrangement provides gradual tissue loading or compression due to the varying sizes of the formed surgical staples $S_1$, $S_2$, thereby minimizing tissue trauma while maintaining a relatively high degree of hemostasis and anastomotic strength.

It is contemplated that to reduce and/or eliminate bleeding and leaks following a surgical stapling procedure, surgical stapler 10 may further include a dispensing tissue reinforcement material, e.g., surgical glue or bio-cement, onto tissue simultaneously with and/or immediately following stapling and cutting of tissue. Incorporating a dispensing mechanism into the stapling assembly promotes uniform application of the glue over the staple line; eliminates the need for instrument exchange, thereby reducing surgical time; and/or enables an efficient use of sealant.

Persons skilled in the art will understand that the structures and methods specifically described herein and shown in the accompanying figures are non-limiting exemplary embodiments, and that the description, disclosure, and figures should be construed merely as exemplary of particular embodiments. For example, the staple cartridge may have a single planar tissue contacting surface and the anvil member may be provided with tissue contacting surface varying in height so as to define more than one tissue gap with respect to the tissue contacting surface of the staple cartridge.

It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical stapling instrument comprising:
an anvil assembly including a planar first tissue contacting surface defining a plurality of staple-forming depressions; and
a cartridge assembly movable relative to the anvil assembly between open and approximated positions, the cartridge assembly including:
a second tissue contacting surface defining a knife channel partitioning the second tissue contacting surface into first and second portions, each of the first and second portions including:
an inner tissue contacting surface disposed adjacent the knife channel and defining a first row of retention slots, the inner tissue contacting surface and the first tissue contacting surface of the anvil assembly defining a first tissue gap; and
an outer tissue contacting surface disposed laterally outward of the respective inner tissue contacting surface and defining a second row of retention slots, the outer tissue contacting surface and the first tissue contacting surface of the anvil assembly defining a second tissue gap larger than the first tissue gap;
a first plurality of staples having a first unformed leg length, the first plurality of staples disposed in the first row of retention slots, the first plurality of staples formed of a first material;
a second plurality of staples having a second unformed leg length longer than the first unformed leg length, the second plurality of staples disposed in the second row of retention slots, the second plurality of staples formed of a second material different from the first material; and
a plurality of pushers, each pusher of the plurality of pushers including first and second panels, the first panel configured to eject one staple of the first plurality of staples through the inner tissue contacting surface, and the second panel configured to eject one staple of the second plurality of staples through the outer tissue contacting surface, each pusher of the plurality of pushers including a base panel interconnecting the first and second panels, wherein the first panel has a length longer than the second panel.

2. The surgical stapling instrument according to claim 1, wherein at least one of the first or second plurality of staples is formed of a permanent or re-absorbable polymer.

3. The surgical stapling instrument according to claim 1, wherein each of the first and second portions of the second tissue contacting surface of the cartridge assembly includes a transitioning portion interconnecting the respective inner and outer tissue contacting surfaces.

4. The surgical stapling instrument according to claim 3, wherein the transitioning portion defines a slope configured to provide gradual compression on tissue when tissue is clamped between the anvil assembly and the cartridge assembly.

5. The surgical stapling instrument according to claim 1, wherein the first tissue contacting surface of the anvil assembly is planar.

6. The surgical stapling instrument according to claim 5, wherein the first tissue contacting surface of the anvil assembly defines a longitudinal channel in registration with the knife channel of the cartridge assembly.

7. The surgical stapling instrument according to claim 1, wherein the inner and outer tissue contacting surfaces of the second tissue contacting surface of the cartridge assembly are symmetric with respect to the knife channel of the cartridge assembly.

8. The surgical stapling instrument according to claim 1, wherein the inner tissue contacting surfaces of the first and second portions of the second tissue contacting surface of the cartridge assembly are coplanar.

9. The surgical stapling instrument according to claim 1, wherein the outer tissue contacting surfaces of the first and second portions of the second tissue contacting surface of the cartridge assembly are coplanar.

10. The surgical stapling instrument according to claim 1, wherein the outer tissue contacting surfaces are parallel to the inner tissue contacting surfaces.

11. The surgical stapling instrument according to claim 1, wherein the second tissue contacting surface of the cartridge assembly and the first tissue contacting surface of the anvil assembly define a varying tissue gap and are configured to apply pressure to tissue disposed therebetween, wherein an amount of pressure applied to a portion of tissue disposed on the inner tissue contacting surface of the cartridge assembly is greater than an amount of pressure applied to a second portion of tissue disposed on the outer tissue contacting surface of the cartridge assembly.

12. A loading unit for use with a powered surgical stapling instrument comprising:
an anvil assembly including a planar anvil surface defining a plurality of staple-forming depressions; and
a cartridge assembly, at least one of the anvil assembly or the cartridge assembly movable relative to the other between an open position and a pre-fire position, the cartridge assembly including:
a tissue contacting surface defining a knife channel, the tissue contacting surface being stepped, the knife channel partitioning the tissue contacting surface into first and second portions, each of the first and second portions including a first tissue contacting surface and a second tissue contacting surface, the first tissue contacting surface including a first plurality of staple retention slots, the first tissue contacting surface and the planar anvil surface configured to apply a first pressure to tissue disposed therebetween in the pre-fire position, the second tissue contacting surface defining a second plurality of staple retention slots, the second tissue contacting surface and the planar anvil surface configured to apply a second pressure to tissue disposed therebetween in the pre-fire position, the second pressure being less than the first pressure;
a first plurality of unformed staples having a first leg length, the first plurality of unformed stapled formed of a first material, the first plurality of unformed staples configured to be ejected through the first plurality of staple retention slots and into engagement with the plurality of staple-forming depressions of the anvil assembly to form a first plurality of formed staples;
a second plurality of unformed staples having a second leg length, the second plurality of unformed staples formed of a second material different from the first material, the second plurality of unformed staples configured to be ejected through the second plurality of staple retention slots and into engagement with the plurality of staple-forming depressions of the anvil assembly to form a second plurality of formed staples, the second leg length being longer than the first leg length; and
a plurality of pushers, each pusher of the plurality of pushers including first and second panels configured to engage a respective one staple of the first plurality of unformed staples and one staple of the second plurality of unformed staples, each pusher of the plurality of pushers including a base panel interconnecting the first and second panels, wherein the first panel has a length longer than the second panel.

13. The loading unit according to claim 12, wherein the second tissue contacting surfaces are disposed laterally outward of the respective first tissue contacting surfaces.

14. The loading unit according to claim 12, wherein each of the first and second portions of the tissue contacting surface of the cartridge assembly includes a transition panel interconnecting the respective first and second tissue contacting surfaces.

* * * * *